United States Patent
Wang et al.

(10) Patent No.: US 8,515,577 B2
(45) Date of Patent: Aug. 20, 2013

(54) MEDICAL TELE-ROBOTIC SYSTEM WITH A MASTER REMOTE STATION WITH AN ARBITRATOR

(76) Inventors: Yulun Wang, Goleta, CA (US); Charles S. Jordan, Santa Barbara, CA (US); Keith Phillip Laby, Santa Barbara, CA (US); Jonathan Southard, Santa Barbara, CA (US)

( * ) Notice: Subject to any disclaimer, the term of this patent is extended or adjusted under 35 U.S.C. 154(b) by 135 days.

(21) Appl. No.: 11/983,058

(22) Filed: Nov. 5, 2007

(65) Prior Publication Data

US 2008/0065268 A1 Mar. 13, 2008

Related U.S. Application Data

(63) Continuation of application No. 10/783,760, filed on Feb. 20, 2004, which is a continuation-in-part of application No. 10/206,457, filed on Jul. 25, 2002, now Pat. No. 6,925,357.

(60) Provisional application No. 60/449,762, filed on Feb. 24, 2003.

(51) Int. Cl.
*G05B 19/04* (2006.01)
*G05B 19/418* (2006.01)

(52) U.S. Cl.
USPC ............... 700/247; 700/13; 700/90; 700/245; 700/248; 700/257; 700/259; 700/260; 700/261; 700/262; 700/264

(58) Field of Classification Search
USPC ............. 701/13, 90, 264, 248, 245, 247, 251, 701/257, 258, 260, 261, 262; 901/1, 14, 901/46; 348/14.01–14.09, 14.11, 14.12, 348/14.13; 709/203, 204; 700/13, 90, 264, 700/248, 245, 247, 257, 259, 260, 261, 262
See application file for complete search history.

(56) References Cited

U.S. PATENT DOCUMENTS

| | | | |
|---|---|---|---|
| 3,821,995 | A | 7/1974 | Aghnides |
| 4,413,693 | A | 11/1983 | Derby |
| 4,471,354 | A | 9/1984 | Smith |

(Continued)

FOREIGN PATENT DOCUMENTS

| | | | |
|---|---|---|---|
| CA | 2289697 A1 | 11/1998 |
| CN | 1554193 A | 12/2004 |

(Continued)

OTHER PUBLICATIONS

F. Ando et al., "A Multimedia Self-service Terminal with Conferencing Functions", 1995, IEEE, pp. 357-362.

(Continued)

*Primary Examiner* — Khoi Tran
*Assistant Examiner* — Jorge Peche
(74) *Attorney, Agent, or Firm* — Irell & Manella, Llp.; Ben J. Yorks

(57) ABSTRACT

A robotic system that includes a mobile robot linked to a plurality of remote stations. One of the remote stations includes an arbitrator that controls access to the robot. Each remote station may be assigned a priority that is used by the arbitrator to determine which station has access to the robot. The arbitrator may include notification and call back mechanisms for sending messages relating to an access request and a granting of access for a remote station.

12 Claims, 10 Drawing Sheets

(56) References Cited

U.S. PATENT DOCUMENTS

| | | | |
|---|---|---|---|
| 4,519,466 A | 5/1985 | Shiraishi | |
| 4,572,594 A | 2/1986 | Schwartz | |
| 4,625,274 A | 11/1986 | Schroeder | |
| 4,638,445 A | 1/1987 | Mattaboni | |
| 4,652,204 A | 3/1987 | Arnett | |
| 4,669,168 A | 6/1987 | Tamura et al. | |
| 4,697,472 A | 10/1987 | Hiyane | |
| 4,709,265 A | 11/1987 | Silverman et al. | |
| 4,733,737 A | 3/1988 | Falamak | |
| 4,751,658 A | 6/1988 | Kadonoff et al. | |
| 4,766,581 A * | 8/1988 | Korn et al. | 369/30.4 |
| 4,777,416 A | 10/1988 | George et al. | |
| 4,797,557 A | 1/1989 | Ohman | |
| 4,803,625 A | 2/1989 | Fu et al. | |
| 4,847,764 A | 7/1989 | Halvorson | |
| 4,875,172 A | 10/1989 | Kanayama | |
| 4,942,512 A * | 7/1990 | Kohno | 700/4 |
| 4,942,538 A | 7/1990 | Yuan et al. | |
| 4,953,159 A | 8/1990 | Hayden et al. | |
| 4,974,607 A | 12/1990 | Miwa | |
| 4,977,971 A | 12/1990 | Crane, III et al. | |
| 5,006,988 A | 4/1991 | Borenstein et al. | |
| 5,040,116 A | 8/1991 | Evans, Jr. et al. | |
| 5,051,906 A | 9/1991 | Evans, Jr. et al. | |
| 5,073,749 A | 12/1991 | Kanayama | |
| 5,084,828 A | 1/1992 | Kaufman et al. | |
| 5,130,794 A | 7/1992 | Ritchey | |
| 5,148,591 A | 9/1992 | Pryor | |
| 5,153,833 A | 10/1992 | Gordon et al. | |
| 5,155,684 A | 10/1992 | Burke et al. | |
| 5,157,491 A * | 10/1992 | Kassatly | 348/14.08 |
| 5,182,641 A | 1/1993 | Diner et al. | |
| 5,186,270 A | 2/1993 | West | |
| 5,193,143 A | 3/1993 | Kaemmerer et al. | |
| 5,217,453 A | 6/1993 | Wilk | |
| 5,224,157 A | 6/1993 | Yamada et al. | |
| 5,230,023 A * | 7/1993 | Nakano | 381/110 |
| 5,231,693 A | 7/1993 | Backes et al. | |
| 5,236,432 A | 8/1993 | Matsen, III et al. | |
| 5,305,427 A | 4/1994 | Nagata | |
| 5,315,287 A | 5/1994 | Sol | |
| 5,319,611 A | 6/1994 | Korba | |
| 5,341,242 A | 8/1994 | Gilboa et al. | |
| 5,341,459 A | 8/1994 | Backes | |
| 5,341,854 A | 8/1994 | Zezulka et al. | |
| 5,347,457 A | 9/1994 | Tanaka et al. | |
| 5,350,033 A | 9/1994 | Kraft | |
| 5,366,896 A | 11/1994 | Margrey | |
| 5,374,879 A | 12/1994 | Pin et al. | |
| 5,417,210 A | 5/1995 | Funda et al. | |
| 5,419,008 A | 5/1995 | West | |
| 5,436,542 A | 7/1995 | Petelin et al. | |
| 5,441,042 A | 8/1995 | Putman | |
| 5,441,047 A | 8/1995 | David et al. | |
| 5,442,728 A | 8/1995 | Kaufman et al. | |
| B15153833 I5 | 8/1995 | Gordon et al. | |
| 5,462,051 A | 10/1995 | Oka et al. | |
| 5,486,853 A | 1/1996 | Baxter et al. | |
| 5,510,832 A | 4/1996 | Garcia | |
| 5,528,289 A | 6/1996 | Cortjens et al. | |
| 5,539,741 A | 7/1996 | Barraclough et al. | |
| 5,544,649 A | 8/1996 | David et al. | |
| 5,550,577 A | 8/1996 | Verbiest et al. | |
| 5,553,609 A | 9/1996 | Chen et al. | |
| 5,572,229 A | 11/1996 | Fisher | |
| 5,572,999 A | 11/1996 | Funda et al. | |
| 5,594,859 A | 1/1997 | Palmer et al. | |
| 5,600,573 A | 2/1997 | Hendricks et al. | |
| 5,630,566 A | 5/1997 | Case | |
| 5,636,218 A | 6/1997 | Ishikawa et al. | |
| 5,652,849 A | 7/1997 | Conway et al. | |
| 5,657,246 A | 8/1997 | Hogan et al. | |
| 5,659,779 A | 8/1997 | Laird et al. | |
| 5,682,199 A | 10/1997 | Lankford | |
| 5,684,695 A | 11/1997 | Bauer | |
| 5,701,904 A | 12/1997 | Simmons et al. | |
| 5,739,657 A | 4/1998 | Takayama et al. | |
| 5,749,058 A | 5/1998 | Hashimoto | |
| 5,749,362 A | 5/1998 | Funda et al. | |
| 5,762,458 A | 6/1998 | Wang et al. | |
| 5,764,731 A | 6/1998 | Yablon | |
| 5,767,897 A | 6/1998 | Howell | |
| 5,786,846 A | 7/1998 | Hiroaki | |
| 5,802,494 A | 9/1998 | Kuno | |
| 5,836,872 A | 11/1998 | Kenet et al. | |
| 5,838,575 A | 11/1998 | Lion | |
| 5,857,534 A | 1/1999 | DeVault et al. | |
| 5,867,653 A | 2/1999 | Aras et al. | |
| 5,871,451 A | 2/1999 | Unger et al. | |
| 5,876,325 A | 3/1999 | Mizuno et al. | |
| 5,911,036 A | 6/1999 | Wright et al. | |
| 5,917,958 A | 6/1999 | Nunally et al. | |
| 5,927,423 A | 7/1999 | Wada et al. | |
| 5,949,758 A | 9/1999 | Kober et al. | |
| 5,954,692 A | 9/1999 | Smith et al. | |
| 5,959,423 A | 9/1999 | Nakanishi et al. | |
| 5,966,130 A | 10/1999 | Benman, Jr. | |
| 5,973,724 A | 10/1999 | Riddle | |
| 5,974,446 A | 10/1999 | Sonnenreich et al. | |
| 5,995,884 A | 11/1999 | Allen et al. | |
| 5,999,977 A | 12/1999 | Riddle | |
| 6,006,946 A | 12/1999 | Williams et al. | |
| 6,036,812 A | 3/2000 | Williams et al. | |
| 6,047,259 A | 4/2000 | Campbell et al. | |
| 6,133,944 A | 10/2000 | Braun et al. | |
| 6,135,228 A | 10/2000 | Asada et al. | |
| 6,148,100 A | 11/2000 | Anderson et al. | |
| 6,170,929 B1 | 1/2001 | Wilson et al. | |
| 6,175,779 B1 | 1/2001 | Barrett | |
| 6,201,984 B1 | 3/2001 | Funda et al. | |
| 6,211,903 B1 | 4/2001 | Bullister | |
| 6,219,587 B1 | 4/2001 | Ahlin et al. | |
| 6,232,735 B1 | 5/2001 | Baba et al. | |
| 6,233,504 B1 | 5/2001 | Das et al. | |
| 6,233,735 B1 | 5/2001 | Ebihara | |
| 6,256,556 B1 * | 7/2001 | Zenke | 700/245 |
| 6,259,806 B1 | 7/2001 | Green | |
| 6,259,956 B1 | 7/2001 | Myers et al. | |
| 6,266,162 B1 | 7/2001 | Okamura et al. | |
| 6,266,577 B1 | 7/2001 | Popp et al. | |
| 6,289,263 B1 | 9/2001 | Mukherjee | |
| 6,292,713 B1 | 9/2001 | Jouppi et al. | |
| 6,304,050 B1 | 10/2001 | Skaar et al. | |
| 6,321,137 B1 * | 11/2001 | De Smet | 700/245 |
| 6,325,756 B1 | 12/2001 | Webb et al. | |
| 6,330,486 B1 | 12/2001 | Padula | |
| 6,330,493 B1 | 12/2001 | Takahashi et al. | |
| 6,346,950 B1 | 2/2002 | Jouppi | |
| 6,346,962 B1 | 2/2002 | Goodridge | |
| 6,369,847 B1 | 4/2002 | James et al. | |
| 6,381,515 B1 | 4/2002 | Inoue et al. | |
| 6,408,230 B2 | 6/2002 | Wada | |
| 6,430,471 B1 | 8/2002 | Kintou et al. | |
| 6,430,475 B2 | 8/2002 | Okamoto et al. | |
| 6,438,457 B1 | 8/2002 | Yokoo et al. | |
| 6,452,915 B1 | 9/2002 | Jorgensen | |
| 6,457,043 B1 | 9/2002 | Kwak et al. | |
| 6,459,955 B1 | 10/2002 | Bartsch et al. | |
| 6,463,352 B1 | 10/2002 | Tadokoro et al. | |
| 6,463,361 B1 | 10/2002 | Wang et al. | |
| 6,466,844 B1 | 10/2002 | Ikeda et al. | |
| 6,468,265 B1 | 10/2002 | Evans et al. | |
| 6,474,434 B1 | 11/2002 | Bech | |
| 6,480,762 B1 | 11/2002 | Uchikubo et al. | |
| 6,491,701 B2 | 12/2002 | Tierney et al. | |
| 6,496,099 B2 | 12/2002 | Wang et al. | |
| 6,496,755 B2 | 12/2002 | Wallach et al. | |
| 6,501,740 B1 | 12/2002 | Sun et al. | |
| 6,507,773 B2 | 1/2003 | Parker et al. | |
| 6,522,906 B1 | 2/2003 | Salisbury et al. | |
| 6,523,629 B1 * | 2/2003 | Buttz et al. | 180/167 |
| 6,526,332 B2 | 2/2003 | Sakamoto et al. | |
| 6,529,765 B1 | 3/2003 | Franck | |
| 6,529,802 B1 | 3/2003 | Kawakita et al. | |

| | | |
|---|---|---|
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu |
| 6,543,899 B2 | 4/2003 | Covannon et al. |
| 6,549,215 B2 | 4/2003 | Jouppi |
| 6,563,533 B1 | 5/2003 | Colby |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,594,269 B1 | 7/2003 | Polcyn |
| 6,594,552 B1 | 7/2003 | Nowlin et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,684,129 B2 | 1/2004 | Salisbury et al. |
| 6,691,000 B2 | 2/2004 | Nagai et al. |
| 6,710,797 B1 | 3/2004 | McNelley et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi et al. |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,656 B1 | 10/2004 | Rosenfeld et al. |
| 6,810,411 B1 | 10/2004 | Coughlin et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 * | 2/2005 | Wang et al. .................. 606/1 |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,958,706 B2 | 10/2005 | Chaco et al. |
| 6,965,394 B2 | 11/2005 | Gutta et al. |
| 6,995,664 B1 | 2/2006 | Darling |
| 7,030,757 B2 | 4/2006 | Matsuhira et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 * | 11/2006 | Wang et al. .................. 700/264 |
| 7,151,982 B2 | 12/2006 | Liff |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 * | 1/2007 | Wang et al. .................. 700/245 |
| 7,161,322 B2 | 1/2007 | Wang et al. |
| 7,162,338 B2 | 1/2007 | Goncalves et al. |
| 7,164,969 B2 | 1/2007 | Wang et al. |
| 7,171,286 B2 | 1/2007 | Wang et al. |
| 7,174,238 B1 | 2/2007 | Zweig |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,227,334 B2 | 6/2007 | Yang et al. |
| 7,256,708 B2 | 8/2007 | Rosenfeld |
| 7,262,573 B2 | 8/2007 | Wang et al. |
| 7,289,883 B2 | 10/2007 | Wang et al. |
| 7,292,912 B2 | 11/2007 | Wang et al. |
| 7,321,807 B2 | 1/2008 | Laski |
| 7,346,429 B2 * | 3/2008 | Goldenberg et al. .......... 700/245 |
| 7,382,399 B1 | 6/2008 | McCall et al. |
| 7,386,730 B2 | 6/2008 | Uchikubo |
| 7,404,140 B2 | 7/2008 | O'Rourke |
| 7,432,949 B2 | 10/2008 | Remy et al. |
| 7,441,953 B2 | 10/2008 | Banks |
| 7,525,281 B2 | 4/2009 | Koyanagi et al. |
| 7,535,486 B2 | 5/2009 | Motomura et al. |
| 7,593,030 B2 | 9/2009 | Wang et al. |
| 7,624,166 B2 | 11/2009 | Foote et al. |
| 7,719,229 B2 | 5/2010 | Kaneko et al. |
| 7,761,185 B2 | 7/2010 | Wang et al. |
| 7,769,492 B2 | 8/2010 | Wang et al. |
| 7,813,836 B2 | 10/2010 | Wang et al. |
| 7,831,575 B2 * | 11/2010 | Trossell et al. .............. 707/705 |
| 7,835,775 B2 | 11/2010 | Sawayama et al. |
| RE42,288 E | 4/2011 | Degioanni |
| 7,924,323 B2 | 4/2011 | Walker et al. |
| 7,982,763 B2 | 7/2011 | King |
| 8,077,963 B2 | 12/2011 | Wang et al. |
| 8,116,910 B2 | 2/2012 | Walters et al. |
| 8,170,241 B2 | 5/2012 | Roe et al. |
| 8,179,418 B2 | 5/2012 | Wright et al. |
| 8,209,051 B2 | 6/2012 | Wang et al. |
| 2001/0002448 A1 | 5/2001 | Wilson |
| 2001/0034475 A1 | 10/2001 | Flach et al. |
| 2001/0034544 A1 | 10/2001 | Mo |
| 2001/0037163 A1 | 11/2001 | Allard |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell et al. |
| 2002/0027597 A1 | 3/2002 | Sachau |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0095238 A1 | 7/2002 | Ahlin et al. |
| 2002/0098879 A1 | 7/2002 | Rheey |
| 2002/0111988 A1 | 8/2002 | Sato |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0030397 A1 | 2/2003 | Simmons |
| 2003/0050733 A1 | 3/2003 | Wang et al. |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0100892 A1 | 5/2003 | Morley et al. |
| 2003/0104806 A1 | 6/2003 | Ruef et al. |
| 2003/0114962 A1 | 6/2003 | Niemeyer et al. |
| 2003/0126361 A1 * | 7/2003 | Slater et al. .................. 711/114 |
| 2003/0135203 A1 | 7/2003 | Wang et al. |
| 2003/0144649 A1 | 7/2003 | Ghodoussi et al. |
| 2003/0151658 A1 | 8/2003 | Smith |
| 2003/0171710 A1 | 9/2003 | Bassuk et al. |
| 2003/0174285 A1 | 9/2003 | Trumbull |
| 2003/0180697 A1 | 9/2003 | Kim et al. |

| | | |
|---|---|---|
| 2003/0199000 A1 | 10/2003 | Valkirs et al. |
| 2003/0206242 A1 | 11/2003 | Choi et al. |
| 2003/0216834 A1 | 11/2003 | Allard |
| 2003/0220541 A1 | 11/2003 | Salisbury et al. |
| 2003/0220715 A1* | 11/2003 | Kneifel et al. ............... 700/248 |
| 2003/0231244 A1 | 12/2003 | Bonilla et al. |
| 2003/0232649 A1 | 12/2003 | Gizis |
| 2004/0010344 A1 | 1/2004 | Hiratsuka |
| 2004/0012362 A1 | 1/2004 | Tsurumi |
| 2004/0013295 A1 | 1/2004 | Sabe et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0078219 A1 | 4/2004 | Kaylor et al. |
| 2004/0080610 A1 | 4/2004 | James et al. |
| 2004/0098167 A1 | 5/2004 | Yi et al. |
| 2004/0102167 A1 | 5/2004 | Shim et al. |
| 2004/0117065 A1 | 6/2004 | Wang et al. |
| 2004/0123158 A1* | 6/2004 | Roskind ............... 713/202 |
| 2004/0135879 A1 | 7/2004 | Stacy et al. |
| 2004/0143421 A1 | 7/2004 | Wang et al. |
| 2004/0148638 A1 | 7/2004 | Weisman et al. |
| 2004/0153211 A1 | 8/2004 | Kamoto et al. |
| 2004/0157612 A1 | 8/2004 | Kim |
| 2004/0167666 A1 | 8/2004 | Wang et al. |
| 2004/0167668 A1 | 8/2004 | Wang et al. |
| 2004/0170300 A1 | 9/2004 | Jouppi |
| 2004/0172301 A1 | 9/2004 | Mihai et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0224676 A1 | 11/2004 | Iseki |
| 2004/0230340 A1 | 11/2004 | Fukuchi et al. |
| 2004/0240981 A1* | 12/2004 | Dothan et al. ............... 414/795.4 |
| 2005/0003330 A1 | 1/2005 | Asgarinejad et al. |
| 2005/0007445 A1 | 1/2005 | Foote et al. |
| 2005/0013149 A1* | 1/2005 | Trossell ............... 365/1 |
| 2005/0021182 A1 | 1/2005 | Wang |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0027567 A1 | 2/2005 | Taha |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0065435 A1 | 3/2005 | Rauch et al. |
| 2005/0065438 A1 | 3/2005 | Miller |
| 2005/0065813 A1 | 3/2005 | Mishelevich et al. |
| 2005/0071046 A1 | 3/2005 | Miyazaki et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0122390 A1 | 6/2005 | Wang et al. |
| 2005/0154265 A1 | 7/2005 | Miro et al. |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0232647 A1 | 10/2005 | Takenaka |
| 2005/0267826 A1 | 12/2005 | Levy et al. |
| 2005/0283414 A1 | 12/2005 | Fernandes et al. |
| 2006/0007943 A1 | 1/2006 | Fellman |
| 2006/0013263 A1 | 1/2006 | Fellman |
| 2006/0013469 A1 | 1/2006 | Wang et al. |
| 2006/0013488 A1 | 1/2006 | Inoue |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0064212 A1 | 3/2006 | Thorne |
| 2006/0074525 A1 | 4/2006 | Close et al. |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0142983 A1 | 6/2006 | Sorensen et al. |
| 2006/0161303 A1 | 7/2006 | Wang et al. |
| 2006/0164546 A1 | 7/2006 | Adachi et al. |
| 2006/0173712 A1 | 8/2006 | Joubert |
| 2006/0178776 A1 | 8/2006 | Feingold et al. |
| 2006/0189393 A1 | 8/2006 | Edery |
| 2006/0195569 A1 | 8/2006 | Barker |
| 2006/0259193 A1 | 11/2006 | Wang et al. |
| 2006/0293788 A1 | 12/2006 | Pogodin |
| 2007/0021871 A1 | 1/2007 | Wang et al. |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0112700 A1 | 5/2007 | Den et al. |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0135967 A1 | 6/2007 | Jung et al. |
| 2007/0142964 A1 | 6/2007 | Abramson |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0199108 A1 | 8/2007 | Angle et al. |
| 2007/0216347 A1 | 9/2007 | Kaneko et al. |
| 2007/0250212 A1 | 10/2007 | Halloran et al. |
| 2007/0262884 A1 | 11/2007 | Goncalves et al. |
| 2007/0273751 A1 | 11/2007 | Sachau |
| 2007/0291109 A1 | 12/2007 | Wang et al. |
| 2007/0291128 A1 | 12/2007 | Wang et al. |
| 2008/0011904 A1 | 1/2008 | Cepollina et al. |
| 2008/0065268 A1 | 3/2008 | Wang et al. |
| 2008/0082211 A1 | 4/2008 | Wang et al. |
| 2008/0126132 A1 | 5/2008 | Warner et al. |
| 2008/0133052 A1 | 6/2008 | Jones et al. |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0255703 A1 | 10/2008 | Wang et al. |
| 2008/0263451 A1 | 10/2008 | Portele et al. |
| 2008/0269949 A1 | 10/2008 | Norman et al. |
| 2008/0281467 A1 | 11/2008 | Pinter |
| 2009/0030552 A1 | 1/2009 | Nakadai et al. |
| 2009/0055023 A1 | 2/2009 | Walters et al. |
| 2009/0070135 A1 | 3/2009 | Parida et al. |
| 2009/0105882 A1 | 4/2009 | Wang et al. |
| 2009/0125147 A1 | 5/2009 | Wang et al. |
| 2009/0237317 A1 | 9/2009 | Rofougaran |
| 2009/0240371 A1 | 9/2009 | Wang et al. |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0019715 A1 | 1/2010 | Roe et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0191375 A1 | 7/2010 | Wright et al. |
| 2010/0268383 A1 | 10/2010 | Wang et al. |
| 2010/0323783 A1 | 12/2010 | Nonaka et al. |
| 2011/0050841 A1 | 3/2011 | Wang et al. |
| 2011/0071702 A1 | 3/2011 | Wang et al. |
| 2011/0172822 A1 | 7/2011 | Ziegler et al. |

| | | |
|---|---|---|
| 2011/0187875 A1 | 8/2011 | Sanchez et al. |
| 2011/0190930 A1 | 8/2011 | Hanrahan et al. |
| 2011/0218674 A1 | 9/2011 | Stuart et al. |
| 2011/0245973 A1 | 10/2011 | Wang et al. |
| 2011/0292193 A1 | 12/2011 | Wang et al. |
| 2011/0301759 A1 | 12/2011 | Wang et al. |
| 2012/0023506 A1 | 1/2012 | Maeckel et al. |
| 2012/0072023 A1 | 3/2012 | Ota |
| 2012/0092157 A1 | 4/2012 | Tran |

FOREIGN PATENT DOCUMENTS

| | | |
|---|---|---|
| CN | 1554985 A | 12/2004 |
| CN | 101106939 A | 1/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 0466492 | 1/1992 |
| EP | 92/488673 A2 | 6/1992 |
| EP | 0981905 B1 | 1/2002 |
| EP | 1262142 A2 | 12/2002 |
| EP | 1536660 A3 | 9/2004 |
| EP | 1536660 A2 | 6/2005 |
| EP | 2005/1573406 A2 | 9/2005 |
| EP | 2005/1584660 A2 | 11/2005 |
| EP | 2007/1791464 A2 | 6/2007 |
| EP | 2007/1800476 A2 | 6/2007 |
| EP | 2007/1856644 A2 | 11/2007 |
| EP | 2008/1928310 A2 | 6/2008 |
| EP | 2009/2027716 A2 | 2/2009 |
| EP | 2010/2145274 A1 | 1/2010 |
| EP | 2010/2214111 A2 | 8/2010 |
| EP | 2010/2263158 A2 | 12/2010 |
| EP | 2011/2300930 A2 | 3/2011 |
| EP | 2011/2342651 A2 | 7/2011 |
| JP | 07213753 | 8/1995 |
| JP | 07248823 | 9/1995 |
| JP | 07-257422 A | 10/1995 |
| JP | 08-084328 A | 3/1996 |
| JP | 96/8320727 A | 12/1996 |
| JP | 09267276 | 10/1997 |
| JP | 10079097 A | 3/1998 |
| JP | 10288689 A | 10/1998 |
| JP | 2000-032319 A | 1/2000 |
| JP | 2000/049800 A | 2/2000 |
| JP | 2000/079587 A | 3/2000 |
| JP | 2000/196876 A | 7/2000 |
| JP | 00235423 | 8/2000 |
| JP | 2001/125641 A | 5/2001 |
| JP | 01147718 | 5/2001 |
| JP | 2001/179663 A | 7/2001 |
| JP | 01198865 | 7/2001 |
| JP | 01198868 | 7/2001 |
| JP | 01199356 | 7/2001 |
| JP | 00188124 | 1/2002 |
| JP | 02000574 | 1/2002 |
| JP | 2002-046088 A | 2/2002 |
| JP | 2002/112970 A | 4/2002 |
| JP | 2002/101333 A | 5/2002 |
| JP | 2002-305743 A | 10/2002 |
| JP | 02355779 | 12/2002 |
| JP | 2004/524824 T | 8/2004 |
| JP | 2004/261941 A | 9/2004 |
| JP | 2004/289379 A | 10/2004 |
| JP | 2005/028066 A | 2/2005 |
| JP | 2005/059170 A | 3/2005 |
| JP | 2006/508806 A | 3/2006 |
| JP | 2006/109094 A | 4/2006 |
| JP | 2006/224294 A | 8/2006 |
| JP | 2006/246026 A | 9/2006 |
| JP | 2007/081646 A | 3/2007 |
| JP | 2010/064154 A | 3/2010 |
| JP | 2010/532109 A | 9/2010 |
| JP | 2010/246954 A | 11/2010 |
| KR | 2006/0037979 A | 5/2006 |
| KR | 2009/0012542 A | 2/2009 |
| KR | 2010/0019479 A | 2/2010 |
| KR | 2010/0139037 A | 12/2010 |
| WO | 93/06690 A1 | 4/1993 |
| WO | WO-9851078 A1 | 11/1998 |
| WO | 99/67067 A2 | 12/1999 |
| WO | 00/33726 A3 | 6/2000 |
| WO | 03/077745 A1 | 9/2003 |
| WO | 2004/008738 A1 | 1/2004 |
| WO | 2004/013029 A2 | 2/2004 |
| WO | 2004/075456 A2 | 9/2004 |
| WO | 2006/012797 A1 | 2/2006 |
| WO | 2006/078611 A1 | 4/2006 |
| WO | 2006044847 A2 | 4/2006 |
| WO | 2007/041295 A1 | 4/2007 |
| WO | 2007/041295 A2 | 4/2007 |
| WO | 2007/041038 A1 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |

OTHER PUBLICATIONS

Baltus et al., "Towards Personal Service Robots for the Elderly", Computer Science and Robotoics.

Bar-Cohen et al., Virtual reality robotic telesurgery simulations using MEMICA haptic system, Mar. 5, 2001, Internet, pp. 1-7.

Bauer, John et al., "Remote telesurgical mentoring: feasibility and efficacy", 2000, IEEE, pp. 1-9.

Brooks, Rodney, Abstracts from Flesh & Machines, How Robots Will Change Us, "Remote Presence", p. 131-147, Feb. 2002.

Celi et al., "The eICU: It's not just telemedicine", Critical Care Medicine, vol. 29, No. 8 (Supplement), Aug. 2001.

Cleary et al., "State of the art in surgical robotics: Clinical applications and technology challenges", Feb. 24, 2002 Internet, pp. 1-26.

CNN, Floating 'droids' to roam space corridors of the future, Jan. 12, 2000, Internet, pp. 1-4.

Davies, "Robotics in Minimally Invasive Surgery", 1995, Internet, pp. 5/1-5/2.

Elhajj et al., "Supermedia in Internet-based telerobotic operations", 2001, Internet, pp. 1-14.

Ellison et al., "Telerounding and Patient Satisfaction Following Surgery".

Goldberg et al., "Collaborative Teleoperation via the Internet", IEEE International Conference on Robotics and Automation, Apr. 2000, San Francisco, California.

Goldman, Lea, "Machine Dreams", Entrepreneurs, Forbes, May 27, 2002.

Gump, Michael D., "Robot Technology Improves VA Pharmacies", 2001, Internet, pp. 1-3.

Harmo et al., "Moving Eye —Interactive Telepresence Over Internet With a Ball Shaped Mobile Robot", 2000.

Hees, William P., "Communications Design for a Remote Presence Robot", Jan. 14, 2002.

Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.

Ivanova, Natali, "Master's thesis: Internet Based Interface for Control of a Mobile Robot", Department of Numerical Analysis and Computer Science.

Kanehiro, Fumio et al., Virtual Humanoid Robot Platform to Develop Controllers of Real Humanoid Robots without Porting, 2001, IEEE, pp. 3217-3276.
Kaplan et al., "An Internet Accessible Telepresence".
Kuzuoka et al., "Can the GestureCam Be a Surrogate?"
Lim, Hun-ok et al., Control to Realize Human-like Walking of a Biped Humanoid Robot, IEEE 2000, pp. 3271-3276.
Loeb, Gerald, "Virtual Visit: Improving Communication for Those Who Need It Most", 2001.
Mack, "Minimally invasive and robotic surgery", 2001, Internet IEEE, pp. 568-572.
Magne Charge—Smart Power for Electric Vehicles, Internet, Jun. 27, 2002.
McCardle et al., "The challenge of utilizing new technology in design education", 2000 Internet, pp. 122-127.
Nakajima et al., "A Multimedia Teleteaching System sing an Electronic Whiteboard for Two-Way Communication of Motion Videos and Chalkboards", 1993, IEEE, pp. 436-441.
Ogata et al., "Development of Emotional Communication Robot: WAMOEBA-2r—Esperimental evaluation . . . ", 2000 IEEE, pp. 175-180.
Ojha, Anad, "An application of Virtual Reality in Rehabilitation", Jan. 1994, IEEE, pp. 4-6.
Paulos et al., "A World Wide Web Telerobotic Remote Environment Browser", http://vive.cs.berkeley.edu/capek, 1995.
Paulos, Eric John, "Personal Tele-Embodiment", Fall 2001.
Paulos, et al. , "Ubiquitous Tele-embodiment: Applications and Implications", International Journal of Human Computer Studies, Jun. 1997, vol. 46, No. 6, pp. 861-877.
Paulos, et al., "Designing Personal Tele-Embodiment", Presented at the IEEE International Conference on Robotics and Animation, Leuven, Belgium, May 20, 1998.
Pin et al., "A New Family of Omnidirectional and Holonomic Wheeled Platforms for Mobile Robots", IEEE, vol. 10, No. 4, Aug. 1994.
Pyxis HELPMATE®, the Trackless Robotic Courier, Internet, 3 pgs.
Robot Hardware Mobile Robotics Research Group, Edinburgh, "Mobile Robotics Research Group", 2000 Internet, pp. 1-2.
Roy et al., "Towards Personal Service Robots for the Elderly", Internet, Mar. 7, 2002.
Sandt, Frederic et al., "Perceptions for a Transport Robot in Public Environments", 1997, IROS '97.
Shimoga et al., Touch and force reflection for telepresence surgery, 1994, IEEE, pp. 1049-1050.
Tendick et al., "Human-Machine Interfaces for Minimally Invasive Surgery", 1997, IEEE, pp. 2771-2776.
Thrun et al, "Probabilistic Algorithms and the Interactive Museum Tour-Guide Robot Minerva", 2000, Internet pp. 1-35.
Tzafestas, et al., "VR-based Teleoperation of a Mobile Robotic Assistant: Progress Report", 2000, Internet, pp. 1-23.
Weiss et al., Telework and video-mediated communication: Importance of real-time, interactive communication for workers with disabilities, 1999, Internet, pp. 1-4.
Yamasaki et al., Applying Personal Robots and Active Interface to Video Conference Systems, 1995, Internet, pp. 243-248.
Yong et al., "Robot task execution with telepresence using virtual reality technology", 1998, Internet, pp. 1-9.
Zipperer, Lorri, "Robotic dispensing system", 1999, Internet, pp. 1-2.
Zorn, Benjamin G., "Ubiquitous Telepresence", http://www.cs.colorado.edu/~zorn/ut/vision/vision.html, Mar. 5, 1996.
"Inventing the Future: 2000 Years of Discovery",*Discovery Channel Canada* (VideoTranscript) Jan. 2, 2000.
"ITU-T H.323 Packet-based multimedia communications", *ITU*, http://www.itu.int/rec/T-REC-H.323-199802-S/en Feb. 1998.
"Mobile Robotics Research Group", *Mobile Robotics Research Group*, Internet Edinburgh 2000 , pp. 1-2.
"National Energy Research Scientific Computing Center, Berkeley Lab's RAGE Telepresence Robot Captures R&D100 Award", http://www.nersc.gov/news/newsroom/RAGE070202.php Jul. 2, 2002.
"Nomad XR4000 Hardware Manual", *Nomadic Technologies, Inc.* Mar. 1999.

"Spawar Systems Center, "Robart"", San Diego, CA, http://web.archive.org/web/*/http://www.nosc.mil/robots/land/robart/robart.html http://web.archive.org/web/19981202205636/http://www.nosc.mil/robots/land/robart/robart.html 1998.
Al-Kassab, "A Review of Telemedicine", *Journal of Telemedicine and Telecare*, vol. 5, Supplement 1 1999.
Android Amusement Corp., "What Marketing Secret . . . Renting Robots from Android Amusement Corp!", (*Advertisement*) 1982.
Applebome, "Planning Domesticated Robots for Tomorrow's Household", *New York Times*, http://www.theoldrobots.com/images17/dc17.JPG Mar. 4, 1982 , 21 and 23.
Bartholomew, "An Apothecary's Pharmacy", http://classes.bnf.fr/ema/grands/034.htm 1230-1240.
Bauer, Jeffrey C. "Service Robots in Health Care: The Evolution of Mechanical Solutions to Human Resource Problems", Jun. 2003.
Bischoff, "Design Concept and Realization of the Humanoid Service Robot HERMES", *Field and Service Robotics*, Springer London 1998 , 485-492.
Blackwell, Gerry "Video: A Wireless LAN Killer App?", *Internet* Apr. 16, 2002 , 1-3.
Breslow, Michael J. "Effect of a multiple-site intensive care unit telemedicine program on clinical and economic outcome an alternative paradigm for intensivist staffing", *Critical Care Med*; vol. 32, No. 1 Jan. 2004 , pp. 31-38.
Candelas, Herias "Flexible virtual and remote laboratory for teaching Robotics", *FORMATEX 2006; Proc. Advance in Control Education* Madrid, Spain Jun. 2006 , 21-23.
Cheetham, Anastasia "Interface Development for a Child's Video Conferencing Robot", 2000 , 1-4.
cnn.com/technology, "Paging R.Robot: Machine helps doctors with patients", *Internet* Sep. 30, 2003 , 1-3.
Crowley, Susan L. "Hello to Our Future", *AARP Bulletin* http://www.cs.cmu.ed/-nursebot/web/press/aarp 99__14/millennium.html Jan. 2000.
Dalton, "Techniques for Web Telerobotics", *PhD Thesis, University of Western Australia* http://telerobot.mech.uwa.edu.au/information.html, http://catalogue.library.uwa.edu.au/search 2001 , 27-62 149-191.
Digiorgio, James "Is Your Emergency Department of the Leading Edge?", *Internet* 2005 , 1-4.
Elhajj, "Synchronization and Control of Supermedia Transmission Via the Internet", *Proceedings of 2001 International Symposium on Intelligent Multimedia Video and Speech Processing*. Hong Kong May 2-4, 2001.
Fels, "Developing a Video-Mediated Communication System for Hospitalized Children", *Telemedicine Journal*, vol. 5,vol. 5, No. 2, 1999.
Fetterman, "Videoconferencing over the Internet", *Internet* 2001 , 1-8.
Fiorini, P. "Health Care Robotics: A Progress Report", *IEEE International Conference on Robotics and Automation*, 1997.
Ghiasi, "A Generic Web-based Teleoperations Architecture: Details and Experience", *SPIE Conference on Telemanipulator and Telepresence Technologies VI* Sep. 1999.
Goldberg, "Desktop Teleoperation via the World Wide Web, Proceedings of the IEEE International Conference on Robotics and Automation", htto://citeseer.ist.osu.edu/cache/oaoers/cs/5/fto:zSzzSzusc.eduzSzoubzSziriszSzraiders.odf/aol 1995 , 654-659.
Goldberg, "More Online Robots, Robots that Manipulate", *Internet*, Updated Aug. 2001 http://ford.ieor.berkeley.edu/ir/robots__a2.html.
Goldenberg, "Telemedicine in Otolaryngology", *American Journal of Otolaryngology* vol. 23,No. 1 2002 , 35-43.
Han, "Construction of an Omnidirectional Mobile Robot Platform Based on Active Dual-Wheel Caster Mechanisms and Development of a Control Simulator", *Kluwer Acedemic Publishers*, vol. 29 Nov. 2000 , 257-275.
Handley "RFC 2327—SDP:Session Description Protocol", http://www.faqs.org/rfcs/rfc2327.html Apr. 1998.
Hanebeck, "ROMAN: a mobile Robotic Assistant for Indoor Service Applications", *Proceedings of the 1997 IEEE/RSJ International Conference on Intelligent Robots and Systems* 1997.

Haule, "Control Scheme for Delayed Teleoperation Tasks", *Proceedings of the Pacific Rim Conference on Communications, Computer and Signal Processing* May 17, 1995.

Holmberg, "Development of a Holonomic Mobile Robot for Mobile Manipulation Tasks", *International Conference on Field and Service Robotics*, Pittsburgh, PA Aug. 1999.

Ishiguro, "Integrating a Perceptual Information Infrastructure with Robotic Avatars: A Framework for Tele-Existence", *Proceeding of IEEE Conference on Intelligent Robots and Systems*.

Jacobs, "TeleRehab: Applying Telemedicine to Outpatient Physical Therapy", 2002.

Jenkins, "Telehealth Advancing Nursing Practice", *Nursing Outlook*, vol. 49, No. 2 Mar./Apr. 2001.

Johanson, "Supporting video-mediated communication over the Internet", *Chalmers University of Technology,Dept of Computer Engineering*, Gothenburg, Sweden 2003.

Jouppi, Norman "First Steps Towards Mutually-Immersive Mobile Telepresence", *CSCW*, 02 New Orleans LA Nov. 16-20, 2002.

Jouppi, "Mutually-Immersive Audio Telepresence", *Audio Engineering Society Convention Paper presented at 113th Convention* Oct. 2002.

Keller, "Raven Interface Project", *Fall 2001*, http://upclose.lrdc.pitt.edu/people/louw_assets/Raven_Slides.pps.

Khatib, "Robots in Human Environments", *Proc. International Conference on Control, Automation, Robotics, and Vision ICRACV2000* Singapore Dec. 2000 , pp. 454-457.

Lane, "Automated Aides", *Newsday*, http://www.cs.cum.edu/nursebot/web/press/nd4380.htm Oct. 17, 2000.

Lee, "A novel method of surgical instruction: International telementoring", *Internet* 1998 , pp. 1-4.

Linebarger, John M. "Concurrency Control Mechanisms for Closely Coupled Collaboration in Multithreaded Virtual Environments", *Presence, Special Issue on Advances in Collaborative VEs* 2004.

Long, "HelpMate Robotics, Inc. (Formerly Transitions Research Corporation) Robot Navigation Technology", *NIST Special Publication* http://www.atp.nist.gov/eao/sp950-1/helpmate.htm Mar. 1999 , 950-1.

Luna, Nancy "Robot a new face on geriatric care", *OC Register* Aug. 6, 2003.

Mair, "Telepresence—The Technology. And Its Economic and Social Implications", *IEEE Technology and Society* 1997.

Martin, Anya "Days Ahead", *Assisted Living Today*, vol. 9 Nov./Dec. 2002 , pp. 19-22.

Meng, "E-Service Robot in Home Healthcare", *Proceedings of the 2000 IEEE/RSJ, International Conference on Intelligent Robots and Systems* 2000 , pp. 832-837.

Michaud, "Introducing Nursebot", *The Boston Globe*, http://www.cs.cmu.edu/nursebot/web/press/globe_3_01/index.html Sep. 11, 2001 , pp. 1-5.

Montemerlo, "Telepresence: Experiments in Next Generation Internet", *CMU Robotics Institute* http://www.ri.cmu.edu/creative/archives.htm (Video/Transcript) Oct. 20, 1998.

Murphy, "Introduction to A1 Robotics", *A Bradford Book* 2000 , 487.

Ogata, "Emotional Communication Robot: WAMOEBA-2R—Emotion Model and Evaluation Experiments", *Internet* 1999 , pp. 1-16.

Oh, "Autonomous Battery Recharging for Indoor Mobile Robots", *Proceedings of Australian Conference on Robotics and Automation* http://users.rsise.anu.edu.au/rsl/rsl_papers/ACRA2000/Auto_Recharge_Paper.pdf 2000.

Orini, ""Health Care Robotics: A Progress Report"", *IEEE International Conference on Robotics and Automation* Apr. 1997 , 1271-1276.

Paulos, "PRoP: Personal Roving Presence", *ACM:CHI Proceedings of CHI '98*, http://www.prop.org/papers/chi98.pdf 1998 , 6.

Paulos, "Video of PRoP 2 at Richmond Field Station", www.prop.org *Printout of Home Page of Website and two-page Transcript of the audio portion of said PRoP Video* May 2001.

Rovetta, "A New Telerobotic Application: Remote Laparoscopic Surgery Using Satellites and and optical fiber Networks for Data Exchange", *International Journal of Robotics Research* Jun. 1, 1996 , pp. 267-279.

Salemi, "MILO: Personal robot platform", *Internet* 2005 , pp. 1-6.

Schaeffer, "Care-O-bot: A System for Assisting Elderly or Disabled Persons in Home Environments", *Proceedings of AAATE-99*, http://morpha.de/download/publications/IPA 1999.

Schulz, "Web Interfaces for Mobile Robots in Public Places", *Robotics & Automation Magazine, IEEE*, vol. 7, Issue 1 Mar. 2000.

Siegwart, "Interacting Mobile Robots on the Web", *Proceedings of the 1999 IEEE International Conference on Robotics and Automation* May 1999.

Simmons, "Xavier: An Autonomous Mobile Robot on the Web", *IEEE Robotics and Automation Magazine* 1999 , pp. 43-48.

Stephenson, Gary "Dr. Robot Tested at Hopkins", *Internet* Aug. 5, 2003 , pp. 1-2.

Stoianovici, "Robotic Tools for Minimally Invasive Urologic Surgery", *Internet* Dec. 2002 , 1-17.

Suplee, "Mastering the Robot", *The Washington Post* http://www.cs.cmu.edu-nursebotlweb/press/wash/index.html Sep. 17, 2000 , p. A01.

Tahboub, Karim A. "Dynamics Analysis and Control of a Holonomic Vehicle With Continously Variable Transmission", *Journal of Dynamic Systems, Measurement and Control ASME* vol. 124 Mar. 2002 , pp. 118-126.

Telepresence Research, Inc.,, "Telepresence Mobile Robot System", http://www.telepresence.com/telepresence-research/TELEROBOT/ Feb. 20, 1995.

Urquhart, Kim "InTouch's robotic Companion 'beams up' healthcare experts", *Medical Device Daily*, vol. 7, No. 39 Feb. 27, 2003 , p. 1,4.

West, "Design of Ball Wheel Mechanisms for Omnidirectional Vehicles with Full Mobility and Invariant Kinematics", *Journal of Mechanical Design* , vol. 119 Jun. 1997 , pp. 153-161.

Yamauchi, "PackBot: A Versatile Platform for Military Robotics", *Internet* 2004 , pp. 1-10.

Zamrazil, Kristie "Telemedicine in Texas: Public Policy Concerns", *House Research Organization Focus Report, Texas House of Representatives*, http://www.hro.house.state.tx.us/focus/telemed.pdf May 5, 2000 , 76-22.

Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.

Brooks, "A Robust Layered Control System for a Mobile Robot," IEEE Journal of Robotics and Automation, 2 (1), Mar. 1986, 10 pgs.

Davis, "Meet iRobot, The Smartest Webcam on Wheels," Wired Magazine, 8.09, http://www.wired.com/wired/archive/8.09/irobot_pr.html, Sep. 2000, 2 pgs.

Dean, et al., "1992 AAAI Robot Exhibition and Competition," AI Magazine, Spring 1993, 10 pgs.

"Defendant VGo Communications, Inc.'s Invalidity Contentions Pursuant to the Feb. 27, 2012 Civil Minute Order", May 2, 2012.

"Defendant-Counterclaimant VGo Communications, Inc.'s Supplemental Invalidity Contentions Pursuant to the Feb. 27, 2012 Civil Minute Order", May 14, 2012.

Dudenhoeffer, et al., "Command and Control Architectures for Autonomous Micro-Robotic Forces", http://www.inl.gov/technicalpublications/Documents/3157051.pdf, Apr. 2001.

Elhajj, "Real-Time Haptic Feedback in Internet-Based Telerobotic Operation", IEEE International Conference on Electro/Information Technology, http://www.egr.msu.edu/~ralab-web/cgi_bin/internet-teleoperation.php, Jun. 2000.

Fels, "Developing a Video-Mediated Communication System for Hospitalized Children", Telemedicine Journal, vol. 5, No. 2, 1999.

Fong, "Collaborative Control: A Robot-Centric Model for Vehicle Teleoperation", The Robotics Institute Carnegie Mellon University, http://web.archive.org/web/20030504040803/www.ricmu.edu/cgi-bin/tech_reports.cgi?year=2001&text=0, Nov. 2001.

Grow, "Office Coworker Robot," Time Magazine, http://www.time.com/time/specials/packages/article/0,28804,1936165_1936255_1936640,00.html, Nov. 19, 2001, 2 pgs.

Itu, "ITU-T H.281 a Far End Camera Control Protocol for Videoconferences using H.224", http://www.itu.int/rec/T-RECH.281-199411-1/en, Nov. 1994.

Itu, "ITU-T H.450.11 Call Intrusion Supplementary Service for H.323", http://www.itu.int/rec/T-RECH.450.11-200103-1/en, Mar. 2001.

Itu, "ITU-T H.450.9 Call Completion Supplementary Services for H.323", http://www.itu.int/rec/T-RECH.450.9-200011-1/en, Nov. 2000.

Knight, et al., "Active Visual Alignment of a Mobile Stereo Camera Platform", Proceedings of the IEEE, International Conference on Robotics and Automation, San Francisco, Apr. 24-28, 2000, pp. 3202-3208.

Metz, "HP Labs", PCMAG.com, http://www.pcmag.com/article2/0,2817,1130820,00.asp, Jul. 1, 2003.

"PictureTel Adds New Features and Functionality to Its Award-Winning Live200 Desktop Videoconferencing System", PR Newswire Association, LLC, Gale, Cengage Learning, http://www.thefreelibrary.com/PictureTel+Adds+New+Features+And+Functionality+To+Its+Award-Winning...-a019512804, Jun. 13, 1997.

PictureTel, "PictureTel Live200 for Windows NT Product Guide", http://support.polycom.com/global/documents/support/user/products/video/live200_live200NT_product_guide.pdf, Nov. 1994.

Pin, et al., "A New Family of Omnidirectional and Holonomic Wheeled Platforms for Mobile Robots", IEEE, vol. 10, No. 4, Aug. 1994.

Roach, "Automatic Call Back Service in SIP", http://tools.ietf.org/pdf/draftroach-sip-acb-00.pdf, Mar. 2000.

Siegwart, "Interacting Mobile Robots on the Web", Proceedings of the 1999 IEEE International Conference on Robotics and Automation, May 1999.

Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.

U.S. Appl. No. 10/783,760, filed Feb. 20, 2004, Wang, et al., 48 pgs.

U.S. Appl. No. 60/449,762, filed Feb. 24, 2003, Wang, et al., 28 pgs.

Weiss, et al., "PEBBLES: A Personal Technology for Meeting Education, Social and Emotional Needs of Hospitalised Children", Personal and Ubiquitous Computing 5, Springer-Verlag London Ltd., 2001, pp. 157-168.

Zambroski, "CMU, Pitt Developing 'nursebot'", http://www.cs.cmu.edu/~nursebot/web/press/tribunereview.html, Oct. 27, 2000.

* cited by examiner

MEDICAL TELE-ROBOTIC SYSTEM WITH A MASTER REMOTE STATION WITH AN ARBITRATOR

REFERENCE TO CROSS-RELATED APPLICATIONS

This application is a continuation of U.S. application Ser. No. 10/783,760 filed Feb. 20, 2004, which is a continuation-in-part of application Ser. No. 10/206,457 filed on Jul. 25, 2002, now U.S. Pat. No. 6,925,357 granted on Aug. 2, 2005, and claims priority to Provisional Application No. 60/449,762 filed on Feb. 24, 2003.

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope which has a camera that allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The platform includes mechanisms to both pivot and raise the camera and monitor. The teleconferencing platform disclosed in the Canadian patent is stationary and cannot move about a building.

Publication Application No. US-2003-0050233-A1 discloses a remote robotic system wherein a plurality of remote stations can control a plurality of robotic arms used to perform a minimally invasive medical procedure. Each remote station can receive a video image provided by the endoscope inserted into the patient. The remote stations are linked to the robotic system by a dedicated communication link.

BRIEF SUMMARY OF THE INVENTION

A robotic system that includes a mobile robot coupled to a first remote station and a second remote station. The second remote station includes an arbitrator that controls access to the robot. The robot includes a camera and a monitor.

DETAILED DESCRIPTION

Disclosed is a robotic system that includes a mobile robot linked to a plurality of remote stations. One of the remote stations includes an arbitrator that controls access to the robot. Each remote station may be assigned a priority that is used by the arbitrator to determine which station has access to the robot. The arbitrator may include notification and call back mechanisms for sending messages relating to an access request and a granting of access for a remote station.

Figure 1:
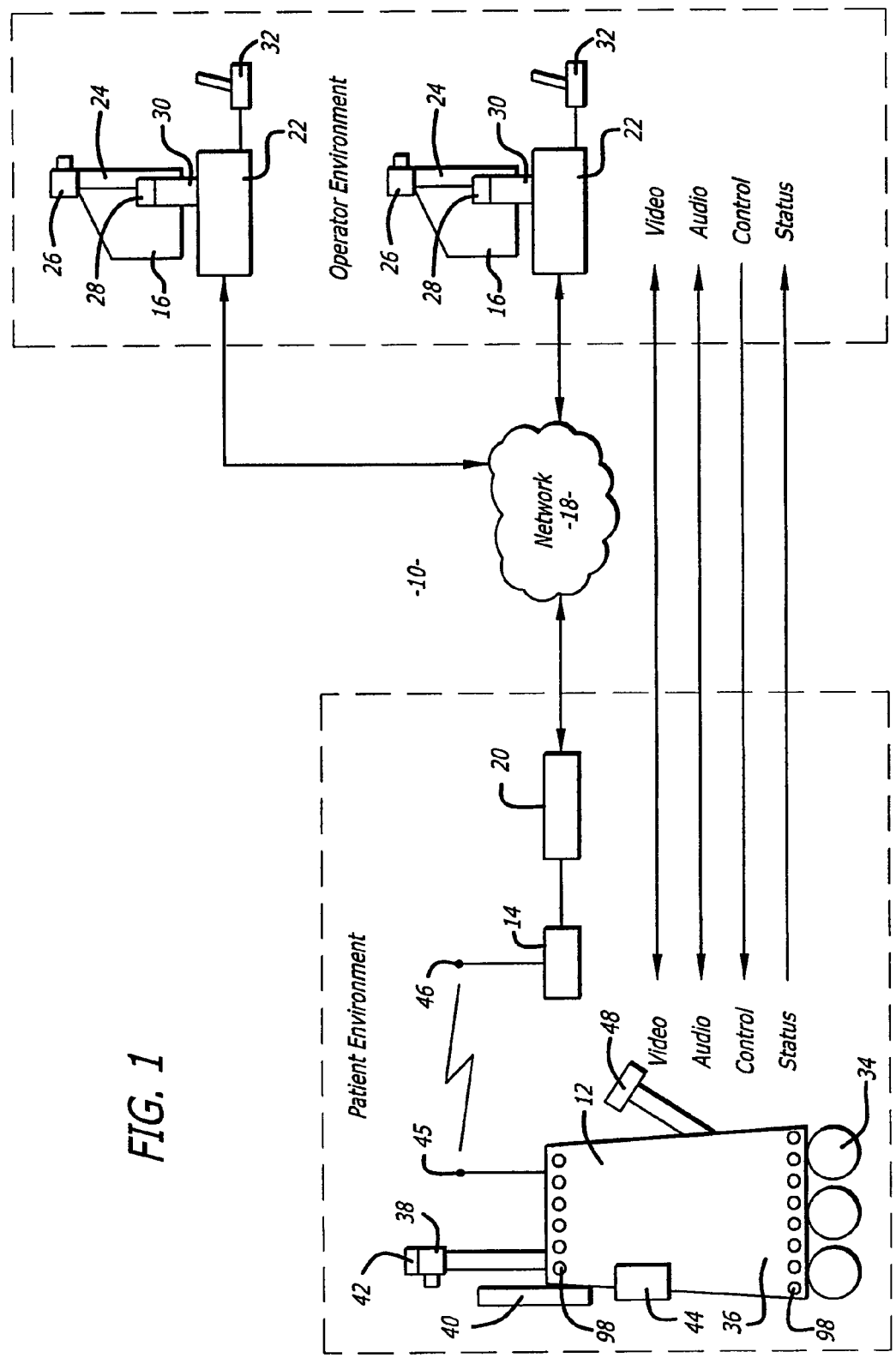
FIG. 1 is an illustration of a robotic system.

Referring to the drawings more particularly by reference numbers, FIG. 1 shows a robotic system 10. The robotic system 10 includes a robot 12, a base station 14 and a plurality of remote control stations 16. Each remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

Each remote control station 16 may include a computer 22 that has a monitor 24, a camera 26, a microphone 28 and a speaker 30. The computer 22 may also contain an input device 32 such as a joystick or a mouse. Each control station 16 is typically located in a place that is remote from the robot 12. Although only one robot 12 is shown, it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user. The robot 12 may further have a handle 48 that can be rotated to a down position which allows someone to manually push or pull the robot 12.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
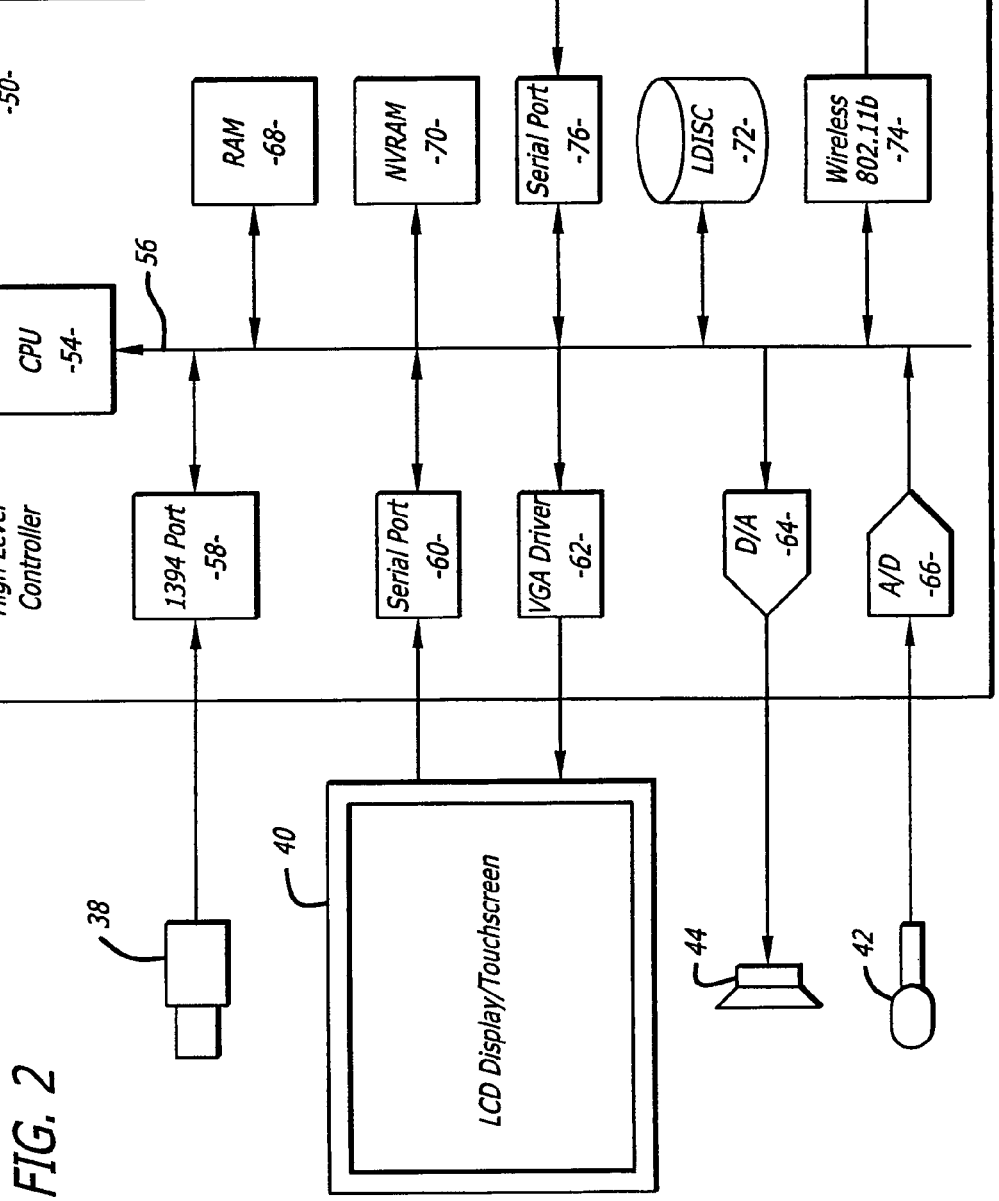
FIG. 2 is a schematic of an electrical system of a robot.
Figure 3:
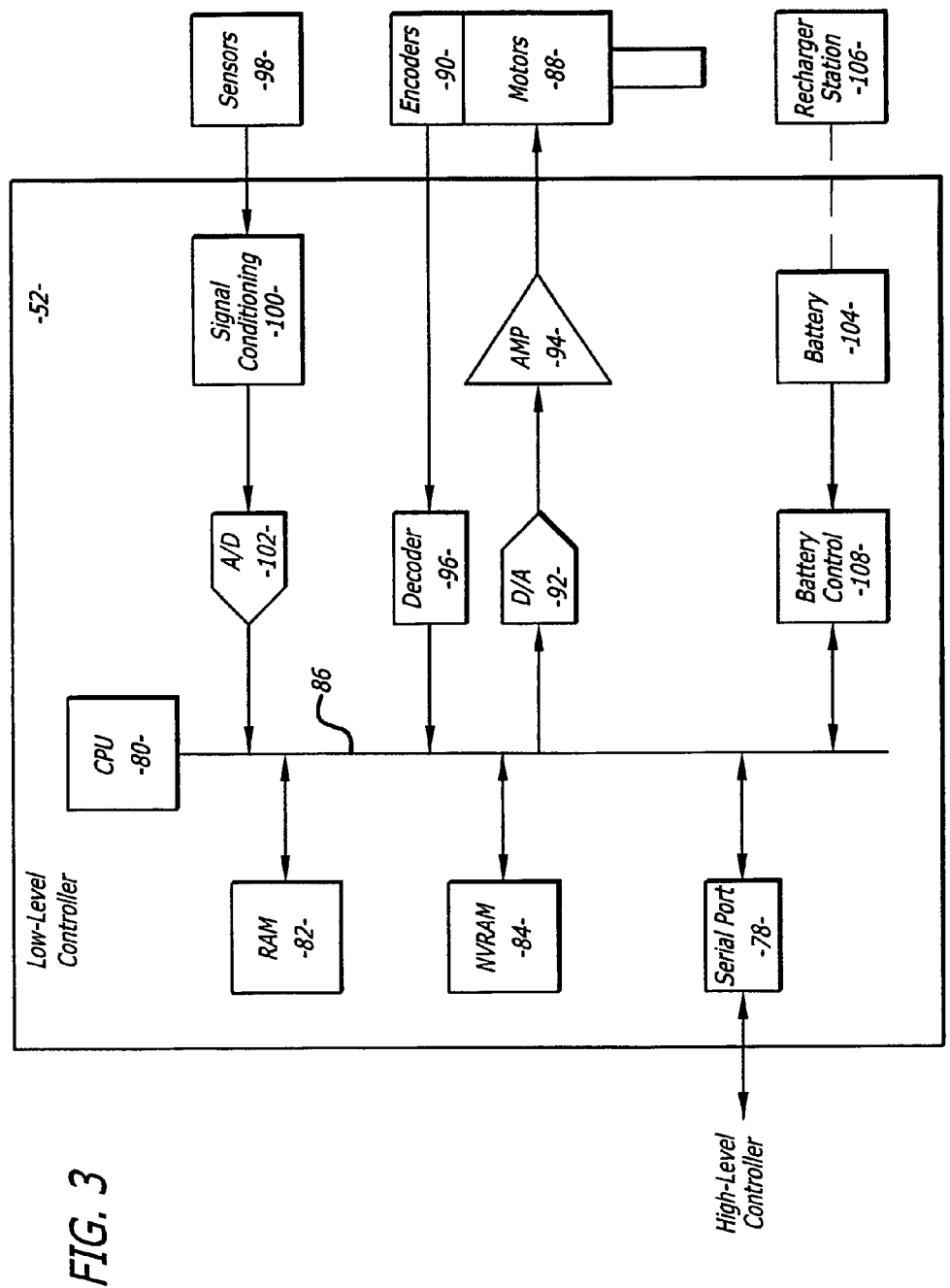
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
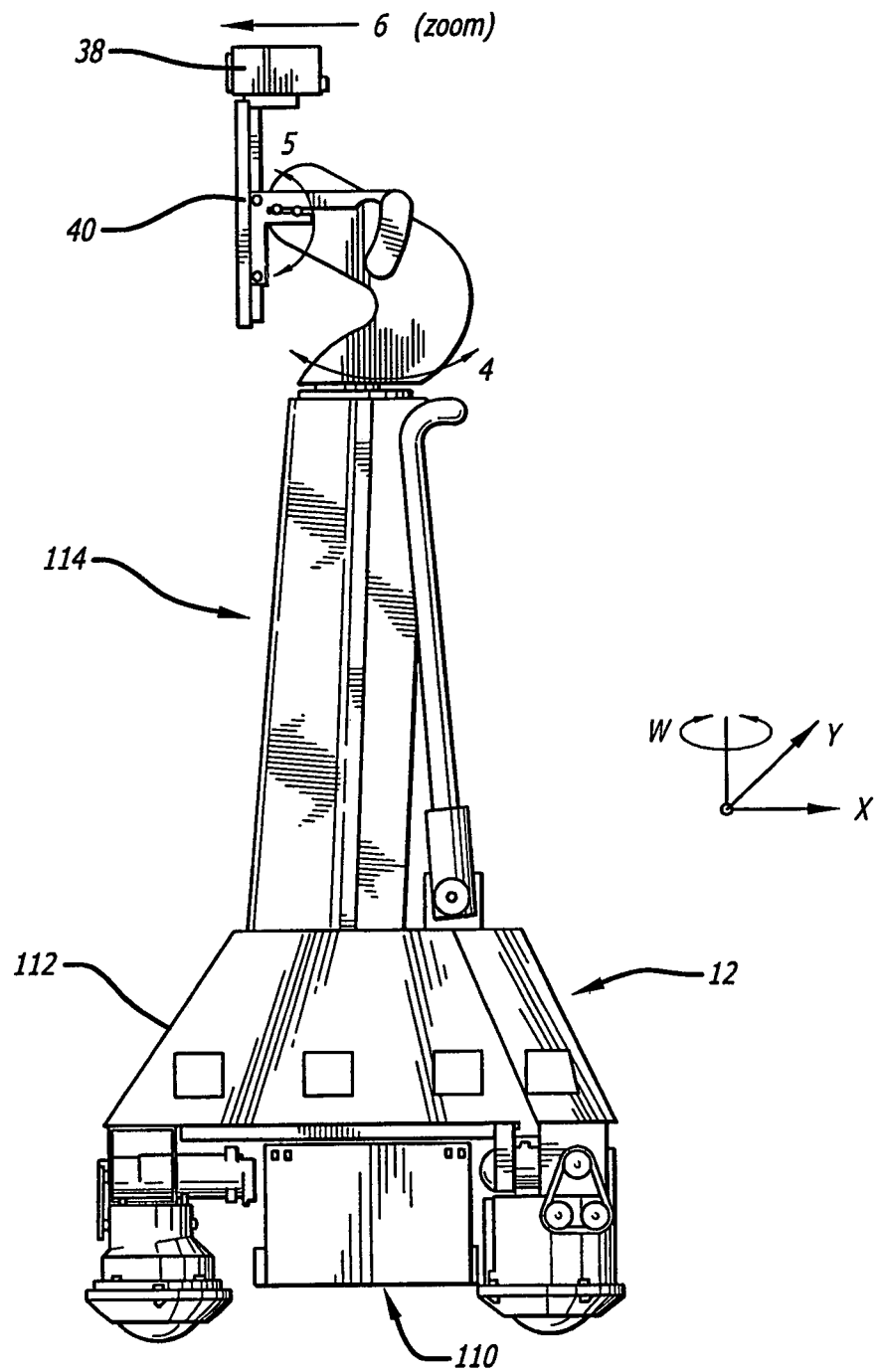
FIG. 4 is side view of the robot.

FIG. 4 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have an pedestal assembly 114 that supports the camera 38 and the monitor 40. The pedestal assembly 114 may have two degrees of freedom so that the camera 26 and monitor 24 can be swiveled and pivoted as indicated by the arrows.

Figure 5:
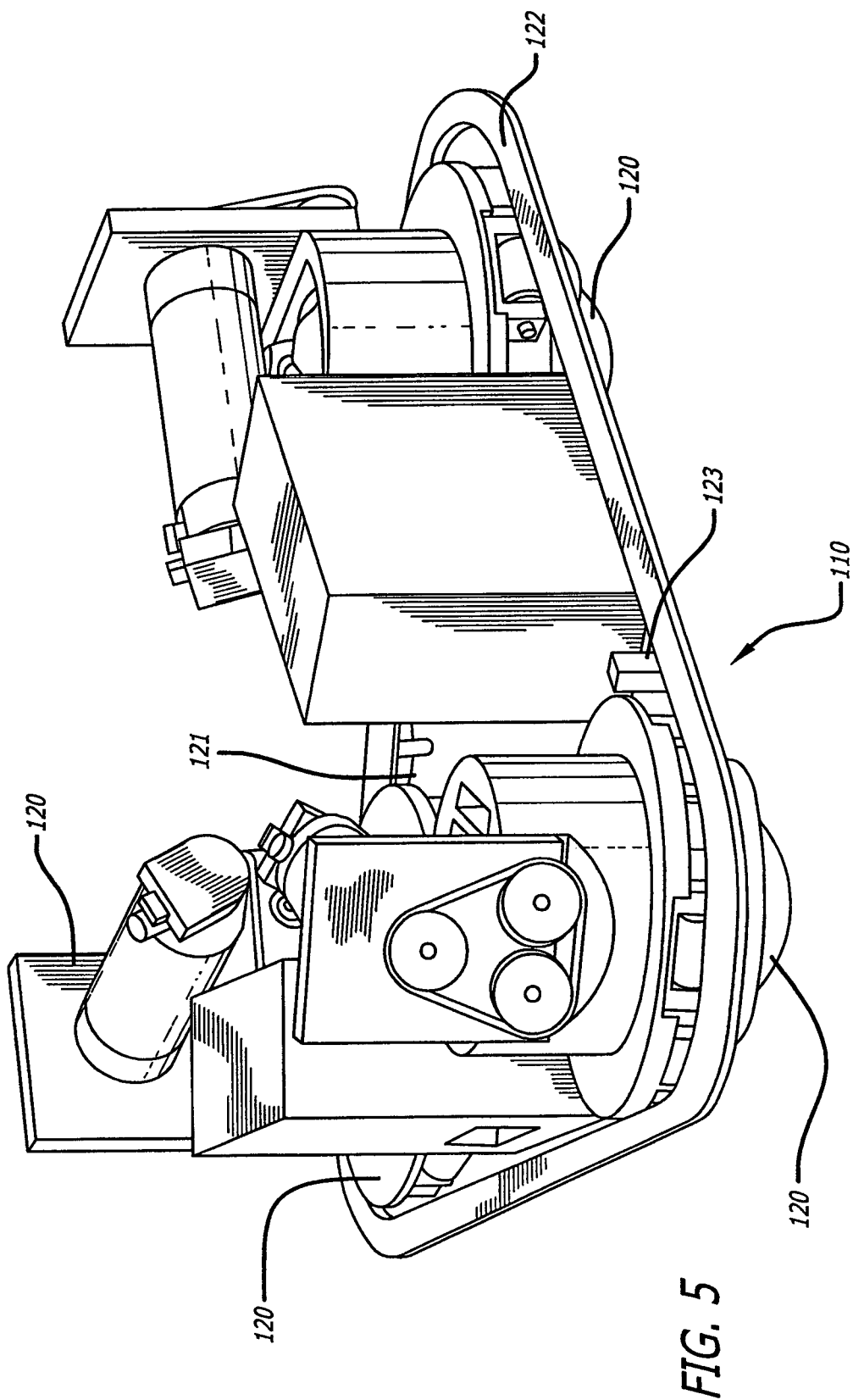
FIG. 5 is a top perspective view of a holonomic platform of the robot.

As shown in FIG. 5 the holonomic platform 110 may include three roller assemblies 120 that are mounted to a base plate 121. The roller assemblies 120 are typically equally spaced about the platform 110 and allow for movement in any direction, although it is to be understood that the assemblies may not be equally spaced.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 6:
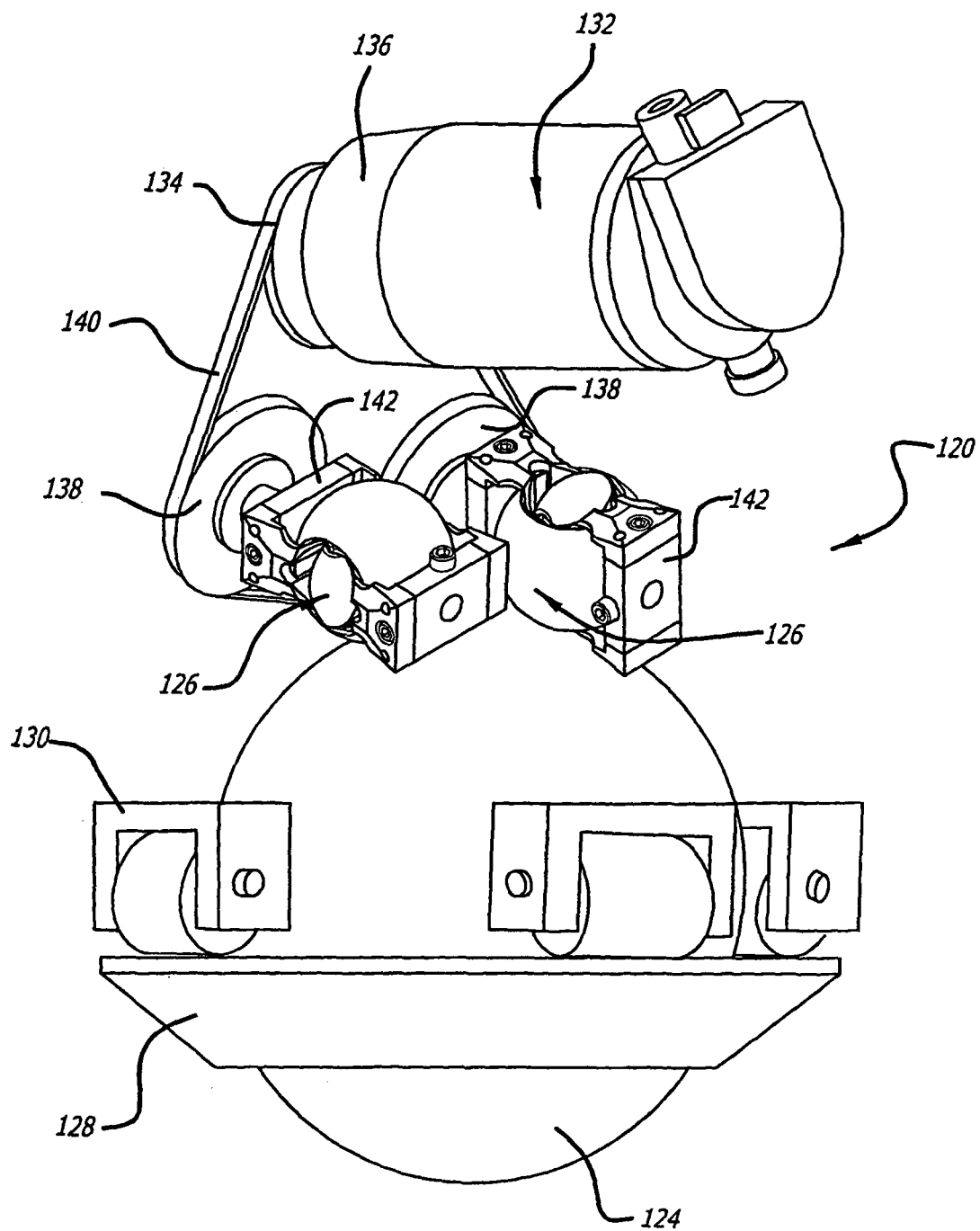
FIG. 6 is a side perspective view of a roller assembly of the holonomic platform.

FIG. 6 shows an embodiment of a roller assembly 120. Each assembly 120 may include a drive ball 124 that is driven by a pair of transmission rollers 126. The assembly 120 may include a retainer ring 128 and a plurality of bushings 130 that captures and allows the ball 124 to rotate in an x and y direction but prevents movement in a z direction. The assembly also holds the ball under the transmission rollers 126.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are each attached to a transmission bracket 142. The transmission rollers 126 are attached to the transmission brackets 142.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The transmission rollers 126 are constructed to always be in contact with the drive ball 124. The brackets 142 allow the transmission rollers 126 to freely spin and allow orthogonal directional passive movement of 124 when one of the other roller assemblies 120 is driving and moving the robot 12.

Figure 7:
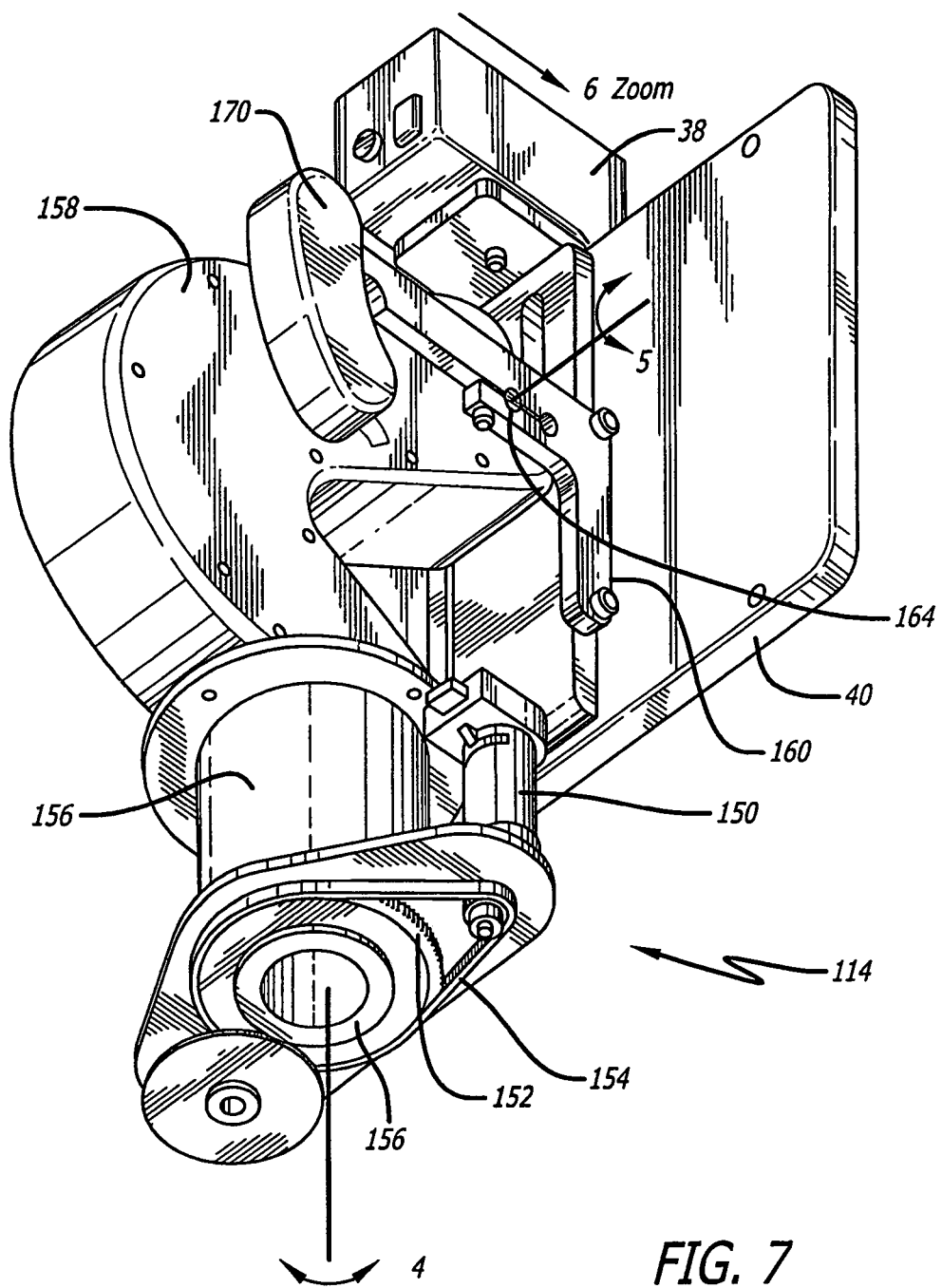
FIG. 7 is a bottom perspective view showing a pedestal assembly of the robot.

As shown in FIG. 7, the pedestal assembly 114 may include a motor 150 that is coupled to a gear 152 by a belt 154. The gear 152 is attached to a shaft 156. The shaft 156 is attached to an arm 158 that is coupled to the camera 38 and monitor 40 by a bracket 160. Activation of the motor 150 rotates the gear 152 and sleeve 156, and causes the camera 38 and monitor 40 to swivel (see also FIG. 4) as indicated by the arrows 4.

Figure 8:
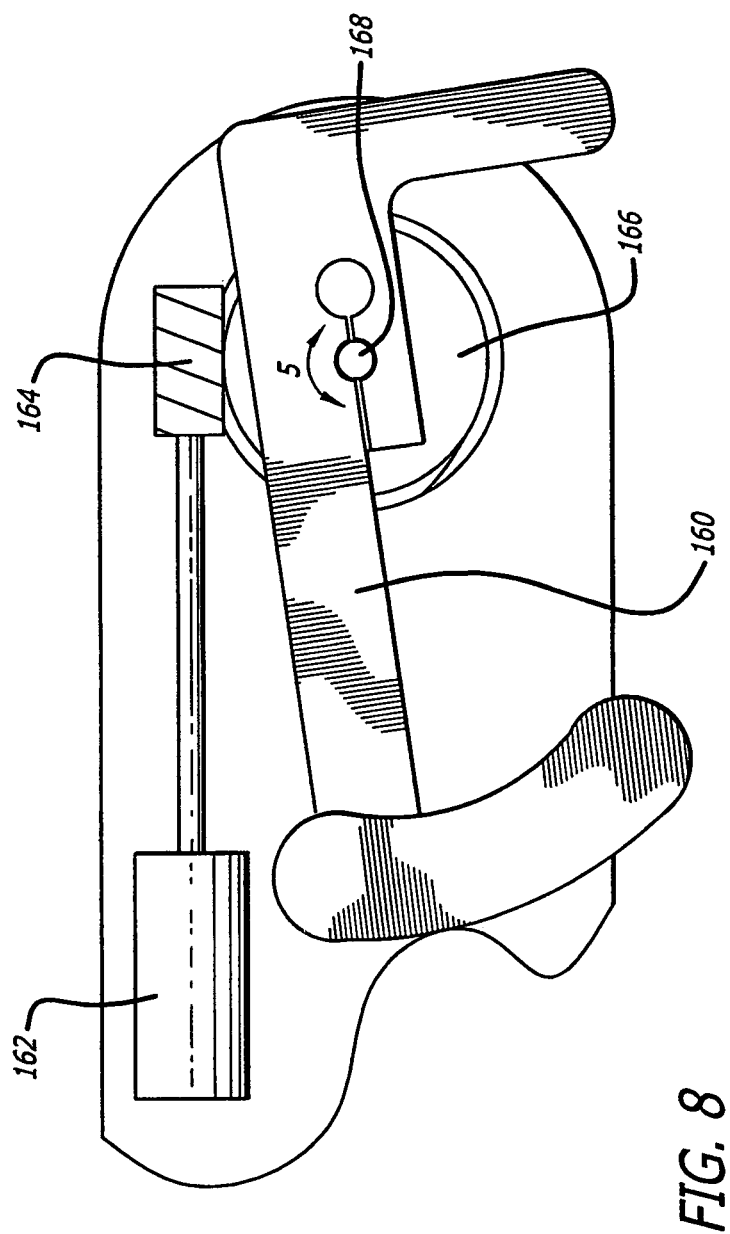
FIG. 8 is a sectional view showing an actuator of the pedestal assembly.

As shown in FIG. 8, the assembly 114 may further include a tilt motor 162 within the arm 158 that can cause the monitor 40 and camera 38 to pivot as indicated by the arrows 5. The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The camera 38 may also include a zoom feature to provide yet another degree of freedom for the operator.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or facility by manipulating the input device 32 at a remote station 16.

Figure 9:
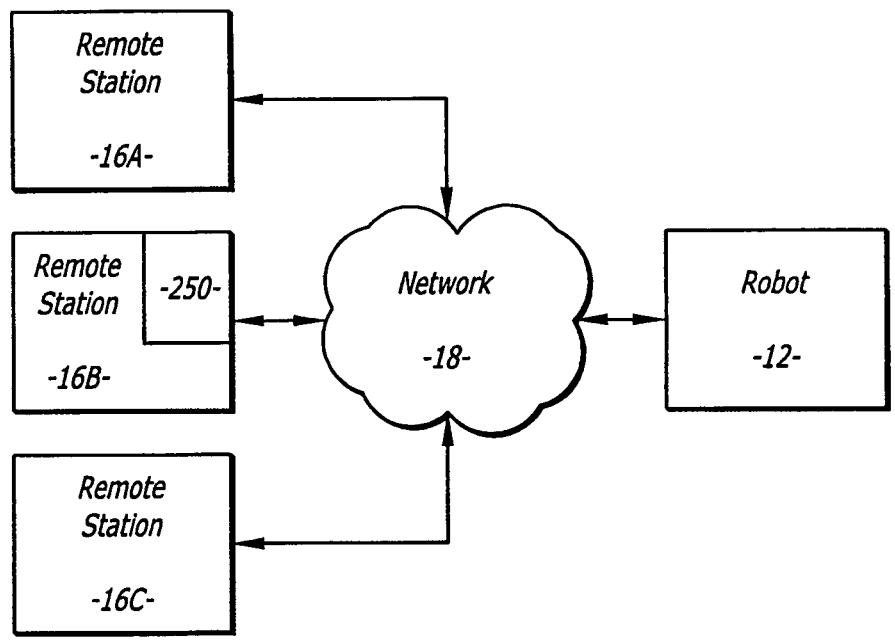
FIG. 9 is a schematic of a robotic system wherein multiple remote stations are coupled to the robot.

FIG. 9 shows a plurality of remote stations 16A-C that can access a robot 12 through a network 18. One of the remote stations 12B can be designated a master station which contains an arbitrator 250. The remote stations 16 may be configured so that all messages, commands, etc. provided to the robot 12 are initially routed to the master remote station 16B. Each message packet may include a priority field that contains the priority number of the station 16A, 16B or 16C sending the message. The arbitrator 250 determines which station has priority and then forwards the message from that station 16A, 16B or 16C to the robot 12. The arbitrator 250 may also send a call back message to the other remote station(s) stating that the station(s) with lower priority does not have access to the robot 12. The arbitrator 250 can cut-off access to the robot from one station and provide access to another station with a higher priority number.

Alternatively, a remote station may route a message, command, etc. to the robot 12 which then forwards a message, command, etc. to the arbitrator 250 to determine whether the station should have access. The arbitrator 250 can then provide a reply message either granting or denying access to the robot.

Figure 10:
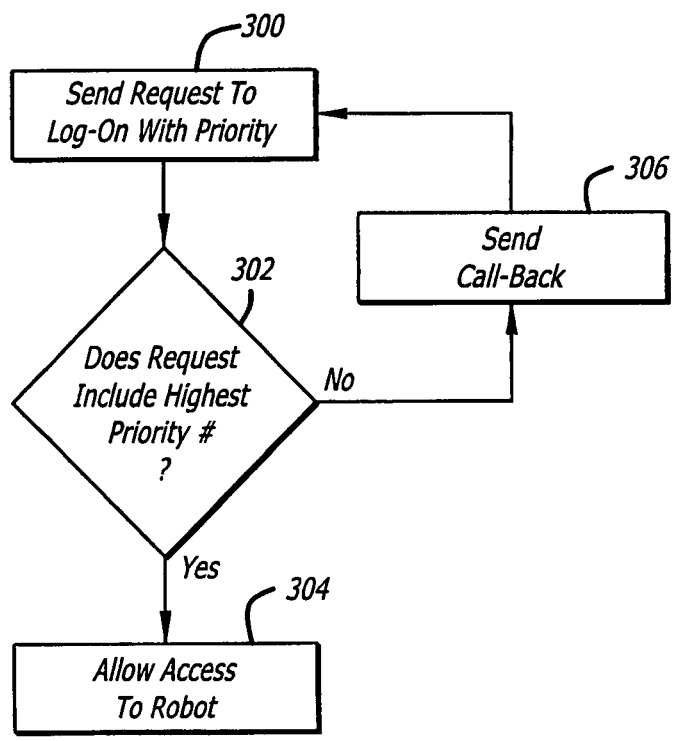
FIG. 10 is a flowchart showing an arbitration scheme for allowing access to the robot.

FIG. 10 shows a flowchart describing a process for access the robot 12. A remote station 16A, 16B or 16C may generate a request message to access the robot in block 300. The message may include the priority number of the remote station. The arbitrator 250 determines whether the request includes a priority number higher than any existing priority number in decision block 302. If a remote station has the same priority number the station first in time maintains access to the robot.

If the request included the highest priority number the arbitrator allows access to the robot in block 304. If the request does not contain the highest priority number, then arbitrator 250 sends a call-back message in block 306. To establish priority, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitrator may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
| --- | --- | --- | --- | --- | --- |
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| | Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| | Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| | Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| | Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 11:
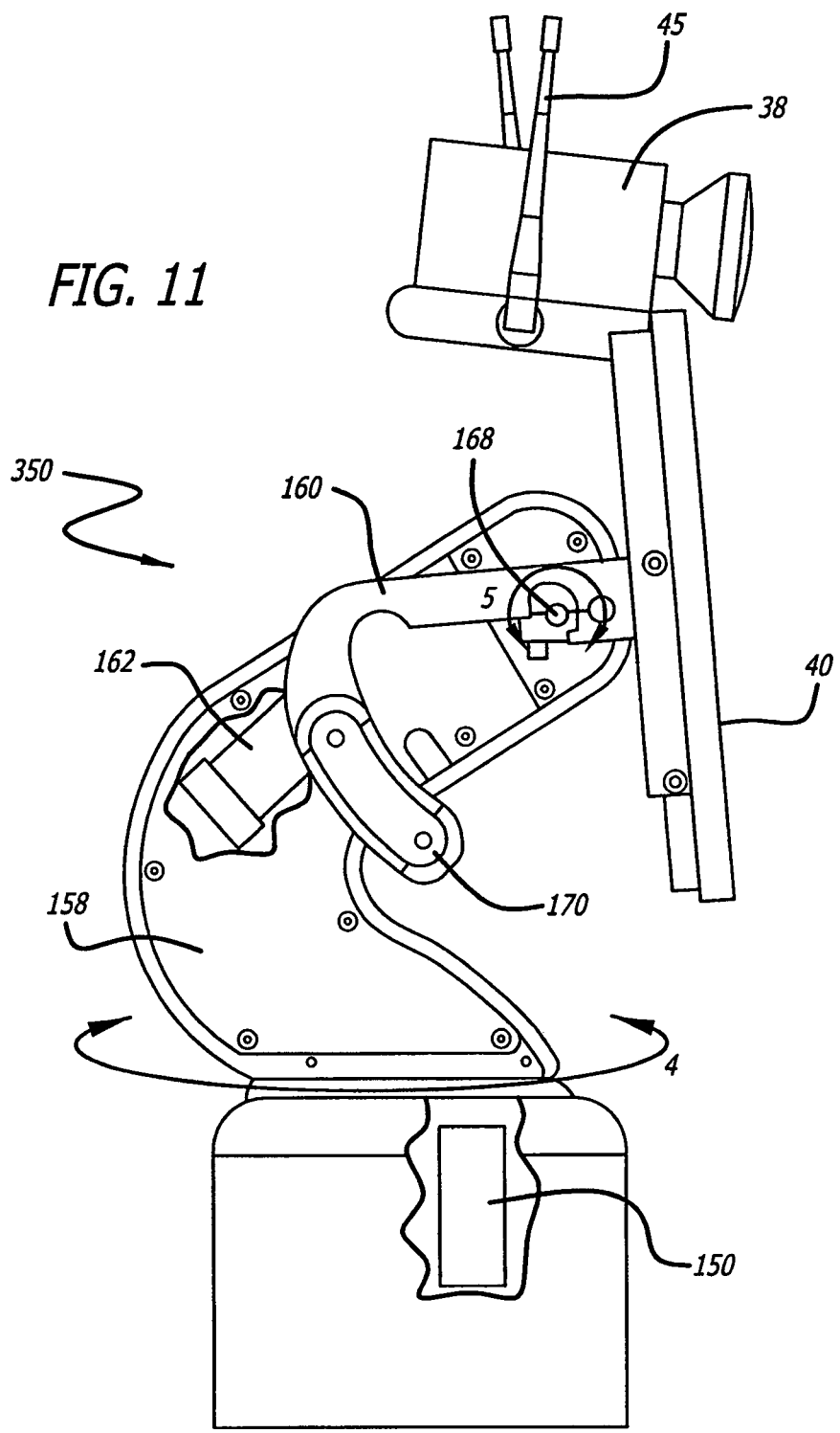
FIG. 11 is a side view of a robot head.

FIG. 11 shows a robot head 350 that can both pivot and spin the camera 38 and the monitor 40. The robot head 350 can be similar to the robot 12 but without the platform 110. The robot head 350 may have the same mechanisms and parts to both pivot the camera 38 and monitor 40 about the pivot axis 4, and spin the camera 38 and monitor 40 about the spin axis 5. The pivot axis may intersect the spin axis. Having a robot head 350 that both pivots and spins provides a wide viewing area. The robot head 350 may be in the system either with or instead of the mobile robot 12.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although the arbitrator is described and shown as being in one of the remote stations, the arbitrator could be within a server, robot or any device, that is connected to the network and in communication with both the remote stations and the robot.

What is claimed is:

1. A robot system, comprising:
a robot that has a camera and a monitor;
a first remote station that has a monitor configured to access and control said robot said first remote station having a first input device operated by a first user to cause movement of said robot;
a second remote station that has a monitor configured to access and control said robot, said second remote station having a second input device operated by a second user to cause movement of said robot; and,
an arbitrator that can operate in an exclusive mode to control access and control movement of said robot exclusively by said first remote station or second remote station, said arbitrator provides a mechanism that allows said first remote station to exclusively access and control movement of said robot, said mechanism denies exclusive access to said robot by said second remote station and notifies the second user that exclusive access to said robot is denied, and subsequent to when request for access is denied notifies the second user that said robot can be exclusively accessed and controlled.

2. The system of claim 1, further comprising a broadband network coupled to said robot and said first and second remote stations.

3. The system of claim 1, wherein said first and second remote stations each, have a priority and said arbitrator provides robot access to said remote station with a highest priority.

4. The system of claim 3, wherein said first and second remote stations may be given priority as a local user, a doctor, a caregiver, a family member, or a service user.

5. The system of claim 1, wherein said arbitrator sends a call back message to inform the user that said robot can be accessed.

6. A robot system, comprising:
a robot that has a camera and a monitor;
a first remote station that has a monitor and is configured to access and control said robot, said first remote station has a first input device operated by a first user to cause movement of said robot; and, a second remote station that has a monitor and is configured to access and control said robot, said second remote station has a second input device operated by a second user to cause movement of said robot; and, arbitration means for operating in an exclusive mode and for allowing exclusive access and control of said robot by said first remote station, denying a request by said second remote station to exclusively access said robot and notifying the second user of said denial, and informing the second user that was previously denied access to said robot, that said robot can be exclusively accessed and controlled.

7. The system of claim 6, further comprising a broadband network coupled to said robot and said first and second remote stations.

8. The system of claim 6, wherein said first and second remote stations each have a priority and said arbitrator provides robot access to said remote station with a highest priority.

9. The system of claim 8, wherein said first and second remote stations may be given priority as a local user, a doctor, a caregiver, a family member, or a service user.

10. The system of claim 6, wherein said arbitrator sends a call back message to inform the user that said robot can be accessed.

11. A method for controlling access to a remote controlled robot, comprising:

providing a robot that has a camera and a monitor;

providing a first remote station that has a monitor and is configured to access and control said robot, said first remote station has a first input device operated by a first user to cause movement of said robot:

providing a second remote station that has a monitor and is configured to access and control said robot, said second remote station has a second input device operated by a second user to cause movement of said robot;

exclusively accessing and controlling the robot by the first remote station;

denying with an arbitrator exclusive access to the robot by the second remote station and notifying the second user of such denial; and, informing with the arbitrator the second user of the second remote station that the robot can be exclusively accessed and controlled.

12. The method of claim 11, wherein the remote station is informed that the robot can be accessed with a call back message.

* * * * *